(12) United States Patent
Locante et al.

(10) Patent No.: US 6,368,108 B1
(45) Date of Patent: Apr. 9, 2002

(54) METHOD FOR IMMEDIATELY PLACING A NON-OCCLUSIVE DENTAL IMPLANT PROSTHESIS

(75) Inventors: William M. Locante, Cordova, TN (US); Robert L. Riley, Vista, CA (US)

(73) Assignee: Sulzer Dental Inc, Carlsbad, CA (US)

( * ) Notice: Subject to any disclaimer, the term of this patent is extended or adjusted under 35 U.S.C. 154(b) by 0 days.

(21) Appl. No.: 09/755,240

(22) Filed: Jan. 5, 2001

(51) Int. Cl.⁷ .................................................. A61C 8/00
(52) U.S. Cl. ........................................................ 433/173
(58) Field of Search .............................. 433/172, 173, 433/174, 175, 176

(56) References Cited

U.S. PATENT DOCUMENTS

| | | | |
|---|---|---|---|
| 5,123,842 A | * | 6/1992 | Roberts ....................... 433/173 |
| 5,967,783 A | | 10/1999 | Ura .............................. 433/174 |

\* cited by examiner

Primary Examiner—Cary O'Connor
(74) Attorney, Agent, or Firm—Philip S. Lyren

(57) ABSTRACT

A method for immediately placing a non-occlusive and non-functional temporary dental implant prosthesis in the jawbone of a human patient.

9 Claims, 3 Drawing Sheets

METHOD FOR IMMEDIATELY PLACING A NON-OCCLUSIVE DENTAL IMPLANT PROSTHESIS

FIELD OF THE INVENTION

The present invention relates generally to a method for immediately placing a non-occlusive and non-functional temporary dental implant prosthesis in the jawbone of a human patient.

BACKGROUND OF THE INVENTION

Numerous surgical techniques and methods currently exist to install a dental implant and prosthesis into the jawbone of a human patient. During a conventional surgical procedure, an incision is made along the gingival tissue at the implant site of the patient, a cylindrical bore is drilled into the alveolar bone, and the bore of the bone is tapped. Once the bore is fully prepared, a dental implant is positioned above the implant site and driven into the bore. A healing screw or healing cap is then placed on the coronal end of the implant, and the gingival tissue is sutured. The implant and healing cap remain within the bone for several months as osseointegration and healing occur. After this healing period, a second surgical procedure begins. During this procedure, the gingival tissue is again cut, the implant is re-exposed, and the healing cap is removed. Thereafter, an abutment is affixed onto the top of the implant and a dental prosthesis is affixed to the abutment.

This conventional surgical procedure has many disadvantages. First, during the healing stage while the implant integrates into the bone, a tooth or dental prosthesis will not be present at the implantation site. The patient may have an unsightly gap or otherwise unaesthetic appearance at this location. Further, in some instances, a metallic healing cap or metallic gingival cuff may be left attached to the implant while the tissue and bone heal. The cap and cuff are often visibly exposed in the mouth of the patient and present an unnatural appearance. Further yet in conventional techniques, the patient has to undergo two separate surgical procedures: an initial procedure to implant the implant and a second procedure to remove the healing cap and attach the abutment and prosthesis. Multiple surgical procedures are costly and not desirable for the patient.

Some dental implant systems and surgical techniques attempt to solve the disadvantages associated with conventional implantation procedures. These systems place a prosthetic tooth in occlusion immediately after the implant is driven and positioned in the jawbone of the patient. In this scenario, the patient has a tooth-like prosthesis immediately after the surgery, so aesthetic appearance is no longer a concern. The prosthesis, however, is left in occlusion and thus exposed to immediate loads.

This procedure has disadvantages too. Preferably, movement and disturbance of the implant should be minimal immediately after it is placed in the jawbone. If the prosthesis and attached implant experience loading too soon, then the position of the implant may rotate, loosen, or otherwise move. Such movement could adversely effect the integration and alignment of the implant.

U.S. Pat. No. 5,967,783 (entitled "Threaded Dental Implant with a Core to Thread Ration Facilitating Immediate Loading and Method of Installation") illustrates a dental implant system designed to immediately place and then load a dental prosthesis. As shown in FIG. 1, an implant 10 consists of an elongated unitary body having a main implant portion 12 with external threads 14 and an extended neck portion 16. One disadvantage to this system is that the implant has an elongated implant and neck portions formed from a single piece. A clinician may be required to perform significant modifications to the extended neck portion so it has the correct height or angle to receive the prosthesis. Further, the neck portion could not easily accommodate a screw-retained prosthesis, especially if the neck needed extensive modification. Further yet, the implant is loaded immediately after it is placed; and such loads, as discussed above, may move the implant or otherwise interfere with its orientation or integration. The external threads 14 on the implant further have a specific and specialized thread pattern to help improve resistance of the implant to chewing and compressive forces. This specialized thread pattern may add additional cost to the implant.

The present invention solves the problems discussed with prior methods and dental delivery systems and provides numerous advantages over these prior systems and methods.

SUMMARY OF THE INVENTION

The present invention is directed toward a method for placing a non-occlusive, non-functional temporary dental implant prosthesis immediately after a dental implant is implanted into the jawbone of a human patient. The implant is placed in a conventional manner for edentulous or extraction dental implantation sites. Thereafter, a separate abutment is connected to the implant; typically such a connection occurs with a screw or cement. A temporary dental implant prosthesis is then attached to the abutment. Most importantly, the temporary prosthesis is placed to be non-occlusive and non-functional; that is to say loads and compressive forces are not transmitted to the implant during normal mastication.

The present method has numerous advantages over prior methods. First, a tooth-shaped temporary prosthesis is connected to implant immediately after the implant is implanted into the jawbone of the patient. As such, the patient does not have an unsightly gap or otherwise unaesthetic appearance at the implantation site. Further, a second, separate surgical procedure is not required since the implant, abutment, and temporary prosthesis are all placed during the first surgical procedure. Further yet, since the prosthesis is left out of occlusion, it is not exposed to immediate loads. Thus, movement and disturbance of the implant is minimized during the integration period. Further yet, the implant and abutment are made from two separate pieces, and the implant is not required to have a special external thread design to help improve resistance of the implant to chewing and compressive forces.

BRIEF DESCRIPTION OF THE DRAWINGS

The invention will hereafter be described with reference to the accompanying drawings.

DESCRIPTION OF THE PREFERRED EMBODIMENTS

Turning to FIG. 2 and FIGS. 3A–3C, the method of the present invention is discussed in detail. Per block 20 of FIG.

2, the invention may be utilized with both edentulous sites and extraction sites. Further, such sites may be single or multiple restorations. For illustrative purposes, the figures and accompanying description teach application of the present invention to a single tooth extraction implantation site.

As shown in block 22, initially the implantation site is evaluated and prepared. Preferably, the site maintains a gentle elevation of the tooth root to preserve the alveolar housing around the extraction site. A periotome or other small elevators (not shown) may be used to release the periodontal ligament or other soft tissue attachment of the tooth to the surrounding bone. Once the tooth is removed, the socket site should be debrided to remove any soft tissue remnants and then irrigated with sterile saline. A visual inspection of the site can aid in determining the appropriate diameter implant.

Figure 1:
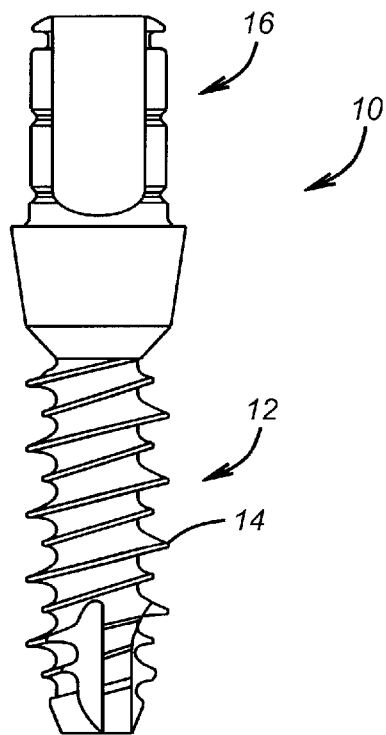
FIG. 1 is a side-view, partially in cross section, of a prior art dental implant system.
Figure 2:
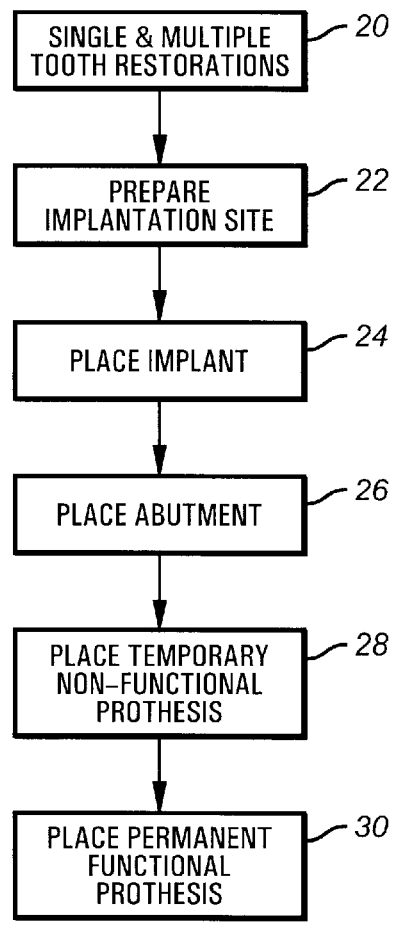
FIG. 2 is a block diagram illustrating the method of the present invention.
Figure 3A:
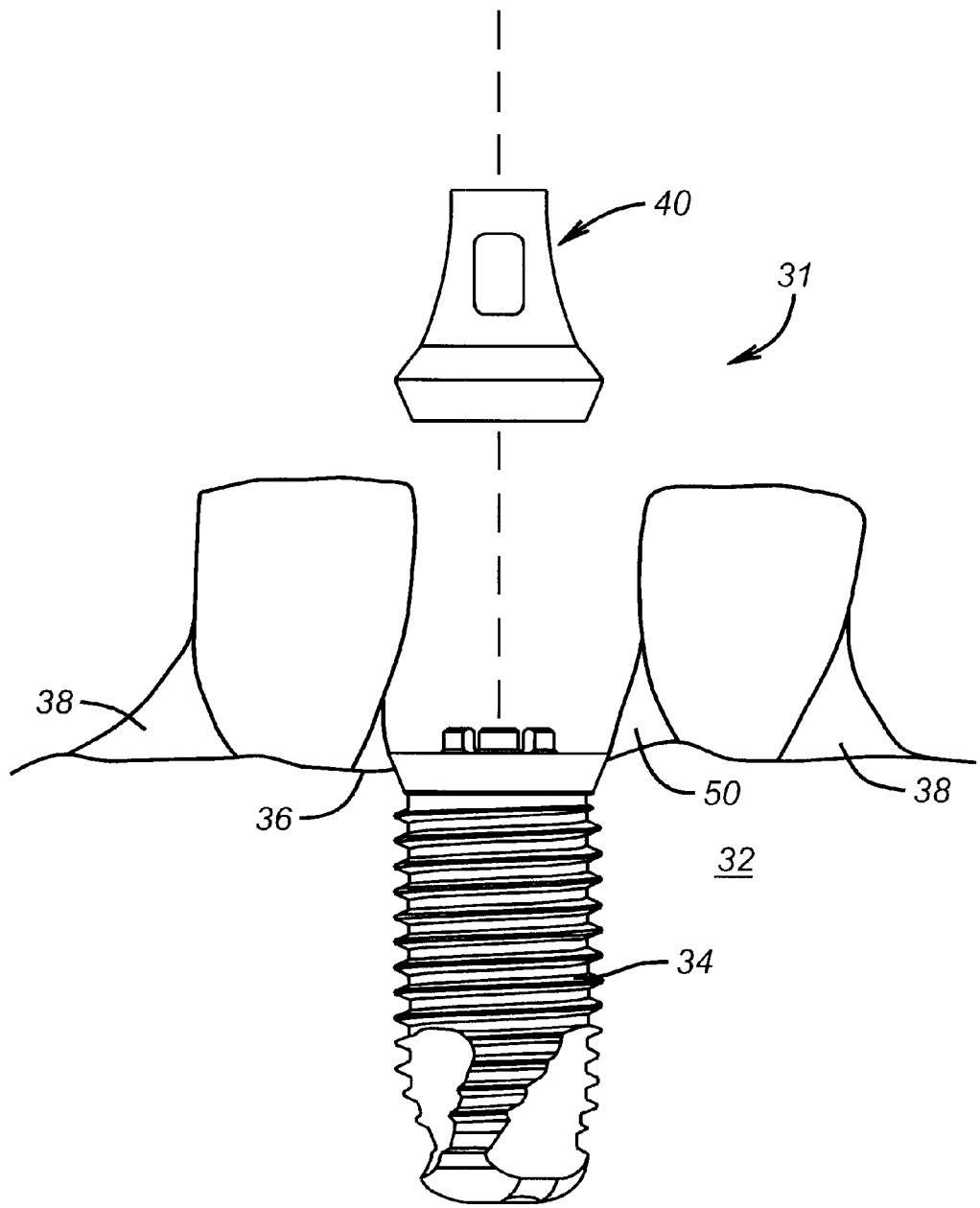
FIGS. 3A–3C show a dental implant, abutment, and temporary prosthesis being implanted according to the method of the present invention.
Figure 3B:
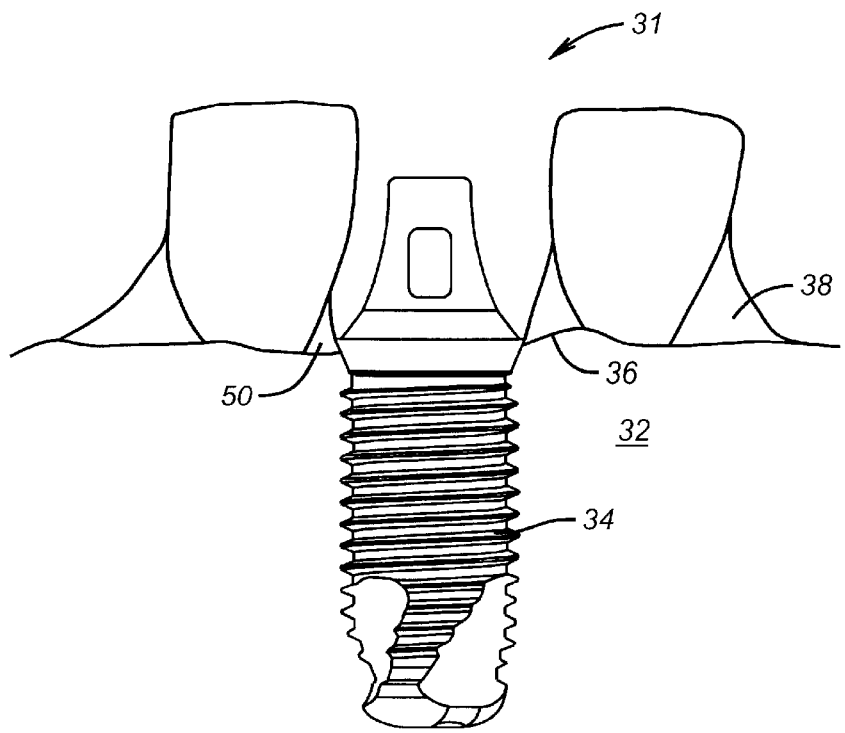
Figure 3C:
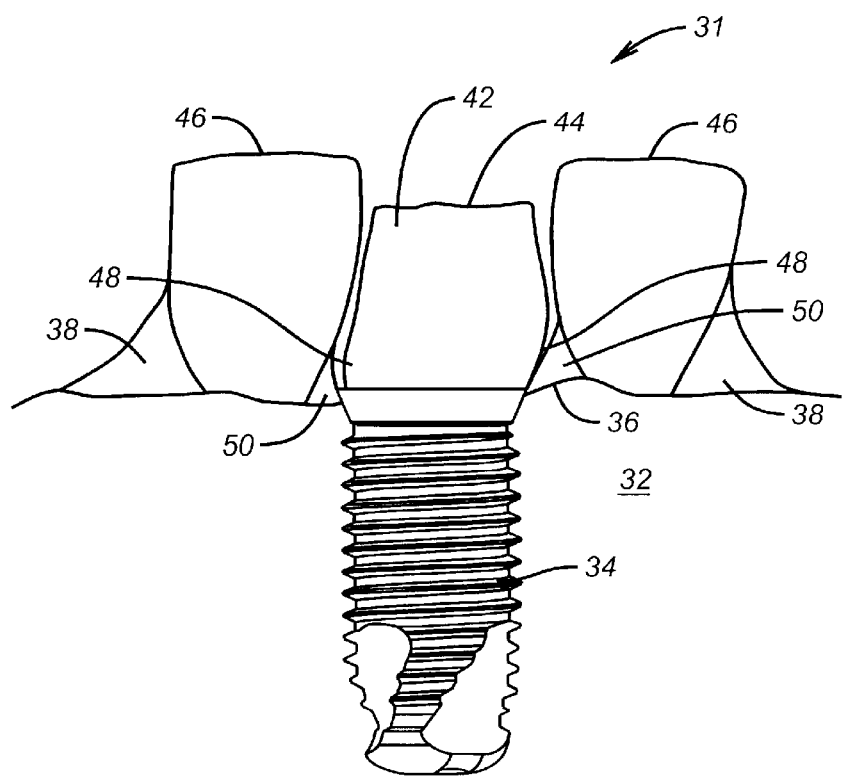

As shown in block 24, the next step is to place the implant into the implantation site 31 (shown in FIGS. 3A–3C). Various implants may be placed using any one of numerous techniques known to those skilled in the art. Preferably, the implant should be dimensioned to sufficiently fill the entire cervical region of the socket. Further, proper orientation and location of the receptor site may be predicated on the initial step of scoring the apex of the socket with a bur or similar instrument. Such scoring provides a recess in the bone 32 to guide a pilot drill (not shown) to a correct, predetermined location.

One example of an implant appropriate for the method of the present invention is a Spline Twist MP-1 implant, manufactured by Sulzer Calcitek Inc. of Carlsbad, Calif. In this instance, the implant 34 can be delivered to the implantation site and inserted via a handpiece and ratchet (not shown). The platform for this implant preferably is placed approximately 1.5 mm below the interproximal bone 36 and below the gingival tissue 38. Placement in this location helps to ensure that the external threads on the implant will be covered by bone and will be at or below the buccal plate.

After the implant is placed, bone grafting may be required. In this instance, a cover screw may be temporarily secured onto the proximal end of the implant to prevent any particulate graft from entering the internal chamber of the implant. Once grafting is completed, the cover screw is removed.

As shown in block 26, the next step is to place an abutment 40 onto the implant. The abutment should be separate from the implant and connectable to the implant using screws, cement, or other techniques known to those skilled in the art. One advantage of having a separate abutment is that various cuff heights and angles may be selected to closely replicate the desired height, angles, and profiles needed. In this manner, the amount of alterations to the abutment is minimized. Of course, the abutment can be modified to meet clinical needs, such as a modification to the overall height or cuff contour.

As shown in block 28, the next step is to place a temporary, non-functional prosthesis 42 on the abutment 40. One important aspect of the present invention is that the prosthesis must be placed in a non-functional or non-occlusive position. Preferably, a top portion 44 of the prosthesis is placed between 0.5 mm and 2 mm below a top 46 of adjacent teeth, as shown in FIG. 3C. In this position, the prosthesis 42 will not be in occlusal loading during the healing period. As such, the prosthesis should be taken completely out of occlusion when the patient is in centric relations and lateral excursions.

After a verification is made that no occlusal loading is present, the prosthesis may be polished and seated with cement or a screw, for example. The patient should be instructed to avoid chewing in the implantation area of the prosthesis while the implant is allowed to heal. Typically, the healing period will occur from about one month to about nine months.

As one important advantage of the method of the present invention, gingival tissue should be contoured around the temporary prosthesis to maintain a natural shape and appearance. Gingival tissue, for instance, can be sutured around a cervical portion 48 of the prosthesis (as shown in FIG. 3C) if the implantation site is edentulous and an incision was made to expose the bone. Suturing the tissue in this manner helps to maintain and develop soft tissue contours around the prosthesis. Suturing, though, may not be necessary if the implantation site is from an extraction and the abutment and temporary prosthesis completely fill the hole left from the natural tooth.

As yet another important advantage of this method, hard and soft tissue contours adjacent to the implant and prosthesis should be maintained to retain interdental papilla 50.

As shown in block 30, after the healing period has elapsed, the temporary prosthesis is removed from the abutment and a permanent prosthesis is connected. The permanent prosthesis is functional and in occlusion in the jawbone of the patient. An experimental trial was conducted on a small group of patients to determine the feasibility of a method in accordance with the present invention. The method was used on 55 patients: 19 males and 36 females. The ages of the males ranged from 26–55 years and females from 17–78 years. All implants were placed from the pre-molar forward. In the male group, one implant was lost due to trauma. In the female group, one implant was mobile after six weeks and required removal. The male patient was removed from the combine group resulting in a total of 54 patients. Survival rate was approximately 98.15%.

Based on analysis of the patients in this trial, the method of the present invention appears to be a very efficacious for replacing missing anterior teeth. Further evaluation is being conducted in a larger population of patients but shows dramatic promise for the effective replacement of lost anterior teeth. This technique has not been employed to posterior teeth beyond the second premolar. It may be effective in these regions as well; however, the increased occlusal force and protection factors must be considered. The following two cases are examples from the experimental trial.

Case I

A 74-year old female had a fractured, non-salvageable first premolar. The tooth was gently elevated, keeping the soft tissue and hard tissue contours intact. There was no elevation of the soft tissue. The socket site was checked to make sure the buccal plate was intact. Direct visualization and palpation were used to identify the inter-septal buccal plate rim. In this case, the site was prepared via harvest instrumentation. The platform of the implant was set approximately 1–1.5 mm below the level on the inter-septal bone; such placement ensured the shoulder of a 2 mm abutment to be approximately 1 mm below the level of gingival cuff rim. This placement also ensured that the soft tissue would be supported to maintain its position and would allow for maximum emergence of the temporary prosthesis (or provisional). The temporary prosthesis was seated with temporary cement and taken out of occlusion. It was then allowed to heal for 16 weeks. After the healing period, this patient was then sent to another doctor for fabrication of the final restoration. The position of the papilla was maintained as well as that of the buccal gingival contour, allowing for maximum tissue esthetics and excellent emergence profile.

Case II

A 47-year old man had tooth #9 that was super-erupted and mobile. Due to his present occupation, aesthetics and a quick remedy were necessary. The tooth was atraumatically removed and the socket site debrided. The position and loss of the gingiva in relation to the adjacent teeth was important here. The implantation site was prepared in a sequential fashion, utilizing drills and hand instrumentation. The implant was then seated in place, positioning the platform approximately 1–1.5 mm below the level of crestal bone. Here, the width of the socket determined the diameter of the implant, and care was taken not to perforate the buccal plate. The abutment was seated to place, the shoulder being approximately 1 mm below the crest of the gingival collar. The temporary prosthesis was placed and positioned to be out of centric occlusion and excursive movement. The tissue and implant was allowed to heal. After the normal healing time had transpired, the implant was restored.

The experimental trial demonstrates numerous advantages to the method of the present invention. First, the patient does not need to wear a removable prosthesis during the healing period. Second, the patient leaves the implantation procedure with a fixed provisional prosthesis or tooth. This fact alleviates any apprehension that the patient may have about the loss of anterior teeth and provides an esthetically pleasing option. Third, preservation of the implantation site's soft and hard tissue contours are maintained, improving the esthetics of the temporary and permanent prostheses. This preservation also allows for the final restoration of soft tissue such that no sutures are required at the surgical site. Further, the patient receives a temporary prosthetic tooth the same day as surgery, and no unsightly gaps or unnatural appearances occur in the mouth of the patient at the implantation site.

What is claimed is:

1. A method for placing a temporary dental prosthesis in the jawbone of a human patient, the method comprising the steps of:

implanting a dental implant into the jawbone of the patient;

connecting a separate dental abutment to a coronal end of the implant;

connecting a temporary prosthesis to the abutment such that the temporary prosthesis is in a non-occlusive and non-functional position approximately 0.5 mm to 2 mm below adjacent teeth in the jawbone of the patient;

leaving the temporary prosthesis connected to the abutment for a healing period between one and nine months;

removing the temporary prosthesis after the healing period; and replacing the temporary prosthesis with a permanent prosthetic tooth that is in an occlusive and functional position in the jawbone.

2. The method according to claim 1 further comprising the step of suturing adjacent gingival tissue around a cervical portion of the temporary prosthesis for developing soft tissue contours.

3. The method according to claim 2 further comprising the step of maintaining hard and soft tissue contours adjacent to the implant and temporary prosthesis to retain interdental papille.

4. A method for placing a dental prosthesis in the jawbone of a human patient, the method comprising the steps of:

implanting a dental implant into the jawbone of the patient;

connecting an abutment to a coronal end of the implant;

connecting a temporary prosthetic tooth to the abutment;

positioning the temporary prosthetic tooth in a non-occlusive and non-functional position;

leaving the temporary prosthetic tooth connected to the abutment for a period between one and nine months; and removing the temporary prosthetic tooth and replacing it with a permanent prosthetic tooth that is in an occlusive and functional position in the jawbone.

5. The method according to claim 4 in which a top of the temporary prosthetic tooth is positioned between 0.5 mm and 2 mm below a top of adjacent teeth.

6. The method according to claim 5 in which no loading occurs on the temporary prosthetic tooth when the patient is in centric relations and lateral excursions.

7. The method according to claim 4 in which no loading occurs on the temporary prosthetic tooth during mastication by the patient.

8. The method according to claim 4 further comprising the step of suturing gingival tissue around the temporary prosthetic tooth to form soft tissue contours.

9. The method according to claim 4 further comprising the step of maintaining hard and soft tissue contours adjacent to the temporary prosthesis to retain interdental papilla.

* * * * *